(12) United States Patent
Ahmed et al.

(10) Patent No.: US 8,722,665 B2
(45) Date of Patent: May 13, 2014

(54) CINNAMIDO-PYRROLO[2,1-C][1,4] BENZODIAZEPINES AS POTENTIAL ANTICANCER AGENTS AND PROCESS FOR THE PREPARATION THEREOF

(75) Inventors: Kamal Ahmed, Hyderabad (IN); Balakishan Gorre, Hyderabad (IN); Ramakrishna Gadupudi, Hyderabad (IN); Sreekanth Kokkonda, Hyderabad (IN); Rajender, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/128,112

(22) PCT Filed: Feb. 27, 2009

(86) PCT No.: PCT/IN2009/000128
§ 371 (c)(1),
(2), (4) Date: Jan. 3, 2012

(87) PCT Pub. No.: WO2010/052732
PCT Pub. Date: May 14, 2010

(65) Prior Publication Data
US 2012/0095213 A1    Apr. 19, 2012

(30) Foreign Application Priority Data

Nov. 7, 2008 (IN) .......................... 2540/DEL/2008

(51) Int. Cl.
*C07D 487/04* (2006.01)
*A61K 31/5517* (2006.01)

(52) U.S. Cl.
USPC .......................................... 514/220; 540/496

(58) Field of Classification Search
USPC .......................................... 540/496; 514/220
See application file for complete search history.

(56) References Cited

FOREIGN PATENT DOCUMENTS

WO        2008/026125 A2    3/2008

OTHER PUBLICATIONS

Ahmed Kamal, et al; "Synthesis of Novel C2 and C2-C8 Linked Pyrrolo[2,1-c][1,4]benzodiazepine-naphthalimide Hybrids as DNA-Binding Agents", Bioorganic & Medicinal Chemistry Letters, vol. 13, pp. 3577-3581, Oct. 20, 2003.
Kurt W. Kohn, et al; "Reaction of Anthramycin with Deoxyribonucleic Acid", J. Molecular Biology, vol. 51, pp. 551-572; Aug. 1970.
David J. Kaplan, et al; "Anthramycin Binding to Deoxyribonucleic Acid-Mitomycin C Complexes. Evidence for Drug-Induced Deoxyribonucleic Acid Conformational Change and Cooperativity in Mitomycin C Binding", Biochemistry, vol. 20, pp. 7572-7580, Dec. 2, 1981.
David E. Thurston, et al; "Synthesis of Sequence-Selective C8-Linked Pyrrolo[2,1-c][1,4]benzodiazepine DNA Interstrand Cross-Linking Agents", J. Org. Chem. vol. 61, pp. 8141-8147, Nov. 15, 1996.
Stephen J. Gregson, et al; "Design, Synthesis, and Evaluation of a Novel Pyrrolobenzodiazepine DNA-Interactive Agent with Highly Effcient Cross-Linking Ability and Potent Cytotoxicity", J. Med. Chem. vol. 44, pp. 737-748, Published on Web Jan. 31, 2001.
Ahmed Kamal, et al; "Design, Synthesis and Evaluation of New Noncross-Linking Pyrrolobenzodiazepine Dimers with Efficient DNA Binding Ability and Potent Antitumor Activity", J. Med. Chem. vol. 45, pp. 4679-4688, Published on Web Sep. 17, 2002.
Takuji Tanaka, et al; "Inhibition of 4-nitroquinoline-1-oxide-induced rat tongue carcinogenesis by the naturally occurring plant phenolics caffeic, ellagic, chlorogenic and ferulic acids", Carcinogenesis, vol. 14, No. 7, pp. 1321-1325, XP009118484; Jul. 1993.
Ahmed Kamal, et al; "Solid-phase synthesis of new pyrrolobenzodiazeping-chalcone conjugates: DNA-binding affinity and anticancer activity", Bioorganic & Medicinal Chemistry Letters, vol. 18, pp. 2434-2439, Available online Mar. 5, 2008.
Laurence H. Hurley, et al; "Pyrrolo(1,4)Benzodiazepine Antitumor Antibiotics In Vitro Interaction of Anthramycin, Sibiromycin and Tomaymycin with DNA Using Specifically Radiolabelled Molecules", Biochimica et Biophysica Acta, vol. 475, pp. 521-535; Apr. 4, 1977.
S. Kunimoto, et al; "Mazethramycin, A New Member of Anthramycin Group Antibiotics", The Journal of Antibiotics, vol. 33, No. 6, pp. 665-667; Jun. 1980.

*Primary Examiner* — Bruck Kifle
(74) *Attorney, Agent, or Firm* — Ladas & Parry LLP

(57) ABSTRACT

The present invention provides a compound of general formulae (8a-i), (11a-i), (14a-i), and (17a-i), useful as potential antitumour agents against human cancer cell lines. The present invention further provides a process for the preparation of Cinnamido-pyrrolo[2,1-c][1,4]benzodiazepines of general formulae (8a-i), (11a-i), (14a-i), and (17a-i).

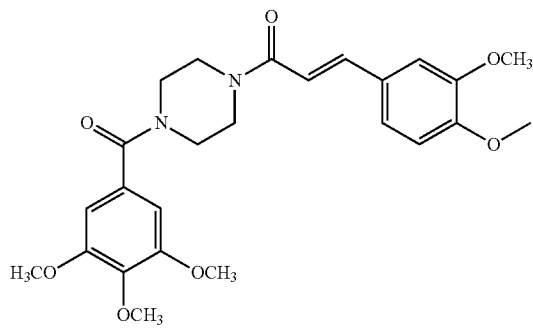

(8a-i)

-continued
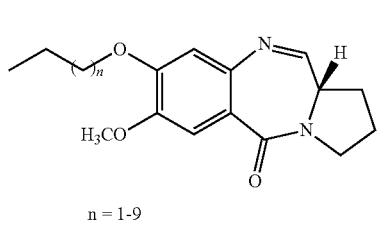
n = 1-9
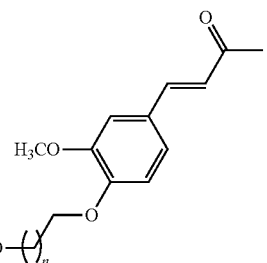
(17a-i)
(11a-i)
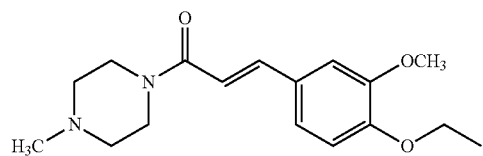
n = 1-9
(14a-i)
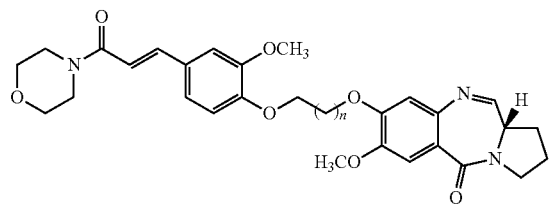
n = 1-9
n = 1-9
3 Claims, No Drawings

CINNAMIDO-PYRROLO[2,1-C][1,4] BENZODIAZEPINES AS POTENTIAL ANTICANCER AGENTS AND PROCESS FOR THE PREPARATION THEREOF

FIELD OF THE INVENTION

The present invention relates to cinnamido-pyrrolo[2,1-c][1,4]benzodiazepines as potential anticancer agents and a process for the preparation there of. Particularly it relates to 7-methoxy-8-{n-(2-methoxy-4-(E)-3-oxo-3-[4-(3,4,5-trimethoxybenzoyl)piperazino]-1-propenyl-phenoxy)alkoxy)}-(11aS) 2,3,5,11a-tetrahydro-5H-pyrrolo[2,1-c][1,4]benzodiazepine-5-one, Formula A

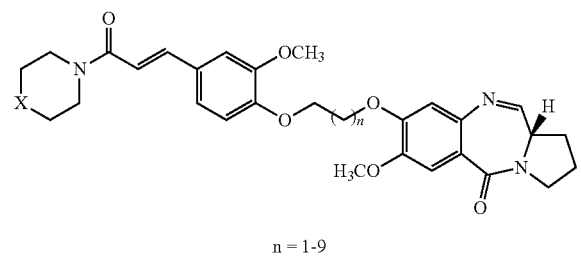

n = 1-9

Wherein X=O or NR

R = —CH₃   R =

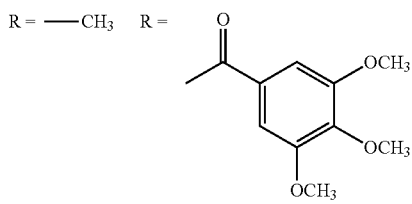

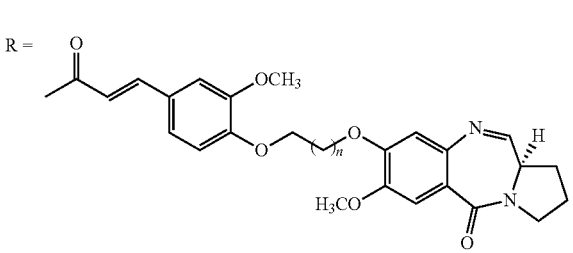

n = 1-9

More particularly, the present invention realtes to 7-methoxy-8-{n-2-methoxy-4-[(E)-3-(4-methylpiperazino)-3-oxo-1-propenylphenoxy]alkoxy}-(11aS)-2,3,5,11a-tetrahydro-5H-pyrrolo[2,1-c][1,4]benzo diazepine-5-one, 7-methoxy-8-{n-2-methoxy-4-[(E)-3-morpholino-3-oxo-1-propenyl phenoxy]alkoxy}-(11aS)-2,3,5,11a-tetrahydro-5H-pyrrolo[2,1-c][1,4]benzo diazepine-5-one and 1,1'-{[(E-3-bis alkoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one with aliphatic chain length variations useful as anticancer (antitumour) agents. The structural formulae of these cinnamido-pyrrolo[2,1-c][1,4]benzodiazepine hybrids is given below.

Formula 8a-i

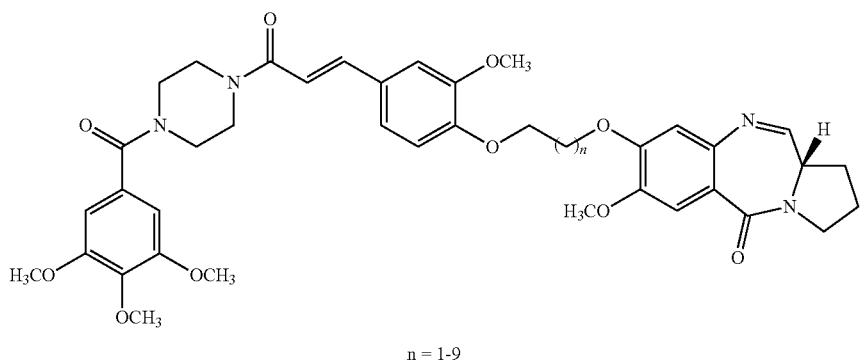

n = 1-9

Formula 11a-i

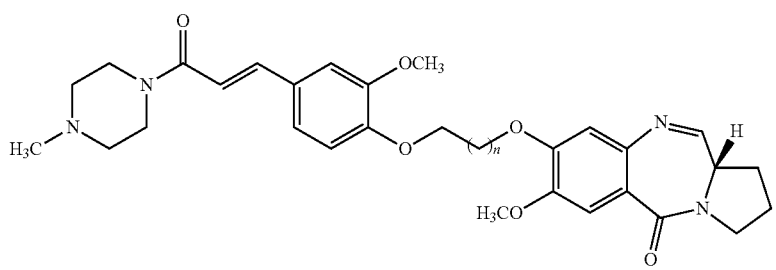

n = 1-9

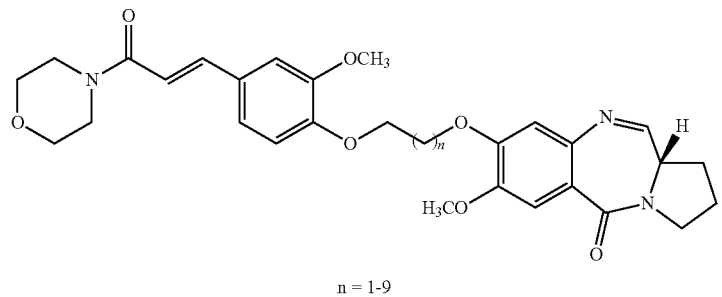

Formula 14a-i n = 1-9

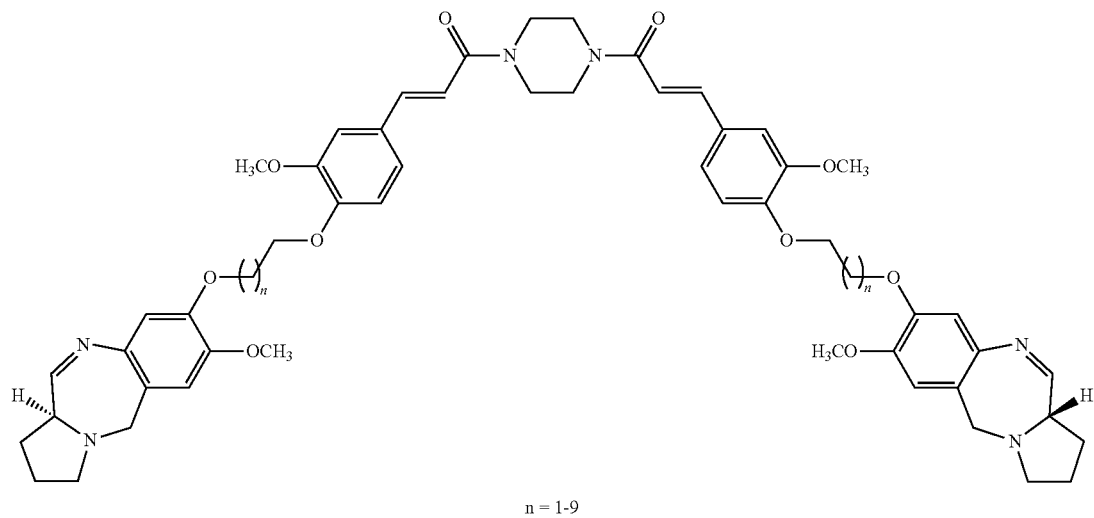

Formula 17a-i n = 1-9

BACKGROUND OF THE INVENTION

Pyrrolo[2,1-c][1,4]benzodiazepine antitumour antibiotics are commonly known as anthramycin class of compounds. In the last few years, a growing interest has been shown in the development of new pyrrolo[2,1-c][1,4]benzodiazepines (PBDs). These antibiotics react covalently with DNA to form an N2-guanine adduct that lies within the minor groove of duplex DNA via an acid-labile aminal bond to the electrophilic imine at the N10-C11 position (Kunimoto, S.; Masuda, T.; Kanbayashi, N.; Hamada, M.; Nagariawa, H.; Miyamoto, M.; Takeuchi, T.; Unezawa, H. *J. Antibiot,* 1980, 33, 665.; Kohn, K. W. and Speous, C. L. *J. Mol. Biol.,* 1970, 51, 551.; Hurley, L. H.; Gairpla, C. and Zmijewski, M. *Biochem. Biophys. Acta.,* 1977, 475, 521.; Kaplan, D. J. and Hurley, L. H. *Biochemistry,* 1981, 20, 7572). The molecules have a right-handed twist, which allows them to follow the curvature of the minor groove of B-form double-stranded DNA spanning three base pairs. A recent development has been the linking of two PBD units through their C-8 positions to give bisfunctional-alkylating agents capable of cross-linking DNA (Thurston, D. E.; Bose, D. S.; Thomson, A. S.; Howard, P. W.; Leoni, A.; Croker, S. J.; Jenkins, T. C.; Neidle, S, and Hurley, L. H. *J. Org. Chem.* 1996, 61, 8141).

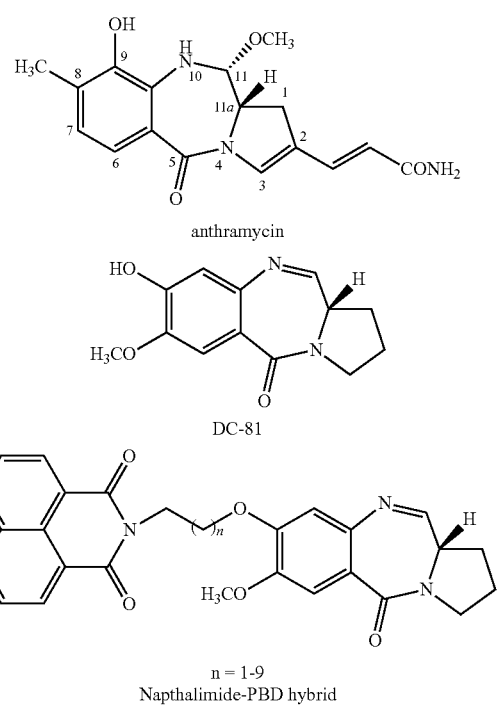

anthramycin

DC-81 n = 1-9
Napthalimide-PBD hybrid

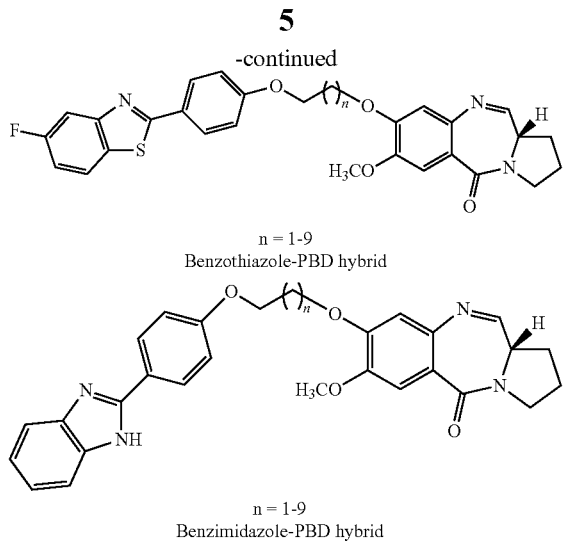

n = 1-9
Benzothiazole-PBD hybrid n = 1-9
Benzimidazole-PBD hybrid

Recently, PBD dimers have been developed that comprise of two C2-exo-methylene substituted DC-81 subunits tethered through their C-8 position via an inert propanedioxy linker (Gregson, S. J.; Howard, P. W.; Hartely, J. A.; Brooks, N. A.; Adams, L. J.; Jenkins, T. C.; Kelland, L. R. and Thurston, D. E. *J. Med. Chem.* 2001, 44, 737). A non-cross-linking mixed imine-amide PBD dimers have been synthesized that have significant DNA binding ability and potent antitumour activity (Kamal, A.; Ramesh, G. Laxman, N.; Ramulu, P.; Srinivas, 0.; Neelima, K.; Kondapi, A. K.; Srinu, V. B.; Nagarajaram, H. M. *J. Med. Chem.* 2002, 45, 4679). Recently, some new pyrrolobenzodiazepine (PBD) hybrids have been synthesized that have significant DNA binding ability and potent antitumour activity. (Kamal, A.; Srinivas, 0.; Ramulu, P.; Ramesh, G.; Kumar, P. P. *Bioorg. Med. Chem. Lett.* 2003, 13, 3577).

Naturally occurring pyrrolo[2,1-c][1,4]benzodiazepines belong to a group of antitumour antibiotics derived from *Streptomyces* species. Recently, there is much impetus for the PBD systems as they can recognize and bind to specific sequence of DNA. Examples of naturally occurring PBDs include anthramycin, DC-81, tomaymycin, sibiromycin and neothramycin.

However, the clinical efficacy for these antibiotics is hindered by several limitations, such as poor water solubility, cardio toxicity, development of drug resistance and metabolic inactivation.

OBJECTIVES OF THE INVENTION

The main objective of the present invention is to provide novel cinnamido-pyrrolo[2,1-c][1,4]benzodiazepines useful as antitumour agents.

Yet another object of this invention is to provide a process for the preparation of novel cinnamido-pyrrolo[2,1-c][1,4]benzodiazepines

SUMMARY OF THE INVENTION

Accordingly the present invention provides a novel cinnamido-pyrrolo[2,1-c][1,4]benzodiazepines of general formulae A Formula A

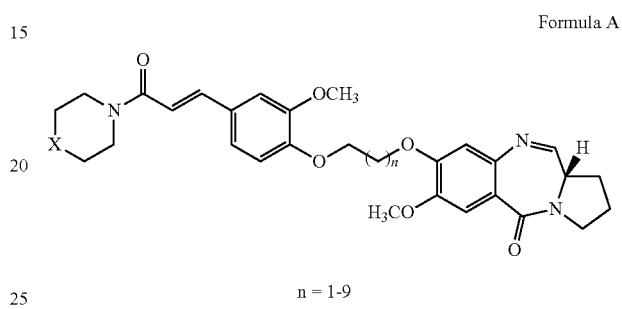

n = 1-9

Wherein X=O or NR

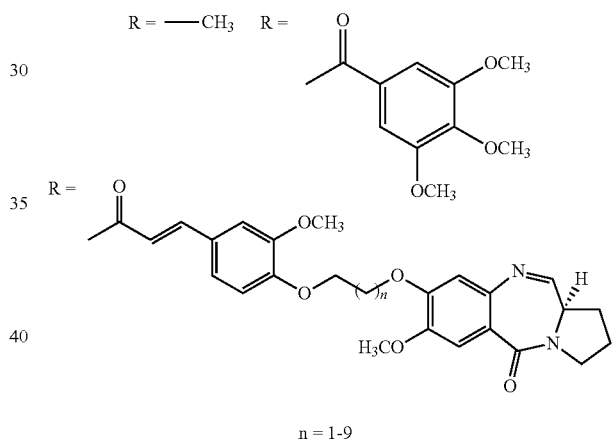

n = 1-9

In an embodiment of the present invention the novel cinnamido-pyrrolo[2,1-c][1,4]benzodiazepines hybrids of formula A is represented by the compounds of general formulae 8a-i, 11a-i, 14a-i and 17a-i.

Formula 8a-i

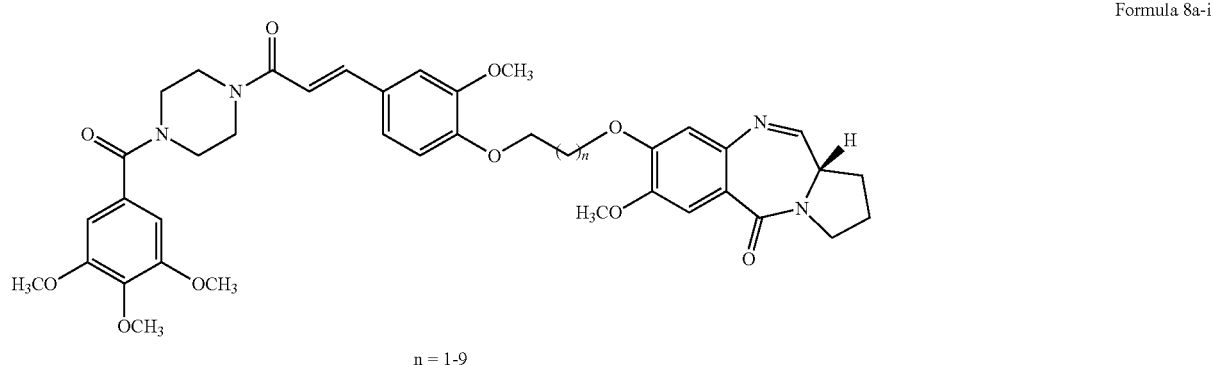

n = 1-9

-continued

Formula 11a-i

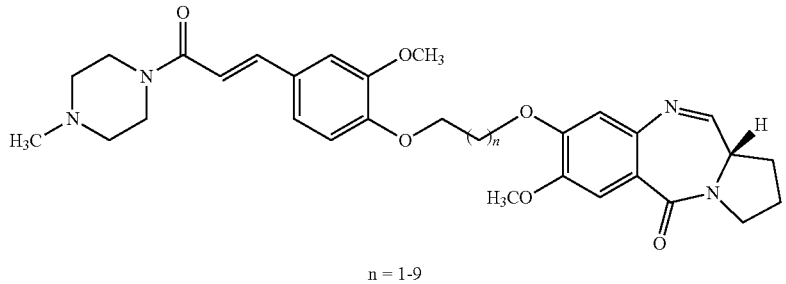

n = 1-9

Formula 14a-i

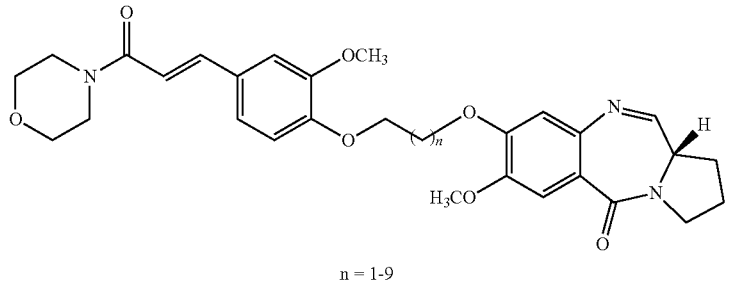

n = 1-9

Formula 17a-i

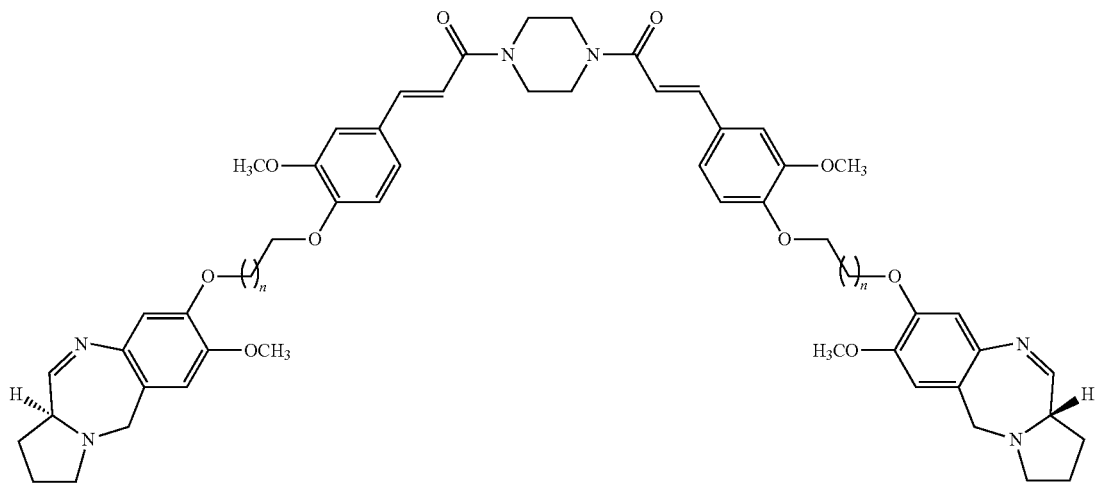

n = 1-9

In yet another embodiment the cinnamido linked pyrrolo [2,1-c][1,4]benzodiazepine hybrids is represented by the group of the following compounds:

7-methoxy-8-{2-(2-methoxy-4-(E)-3-oxo-3-[4-(3,4,5-tri-methoxybenzoyl)piperazino]-1-propenylphenoxy)ethoxy}-(11aS)-2,3,5,11$^a$-tetrahydro-5H-pyrrolo[2,1-c][1,4]benzo-diazepine-5-one (8$^a$);

7-methoxy-8-{3-(2-methoxy-4-(E)-3-oxo-3-[4-(3,4,5-tri-methoxybenzoyl)piperazino]-1-propenylphenoxy)propoxy}-(11aS)-2,3,5,11$^a$-tetrahydro-5H-pyrrolo[2,1-c][1,4]benzo-diazepine-5-one (8b);

7-methoxy-8-{4-(2-methoxy-4-(E)-3-oxo-3-[4-(3,4,5-tri-methoxybenzoyl)piperazino]-1-propenylphenoxy)butoxy}-(11aS)-2,3,5,11$^a$-tetrahydro-5H-pyrrolo[2,1-c][1,4]benzo-diazepine-5-one (8c);

7-methoxy-8-{5-(2-methoxy-4-(E)-3-oxo-3-[4-(3,4,5-tri-methoxybenzoyl)piperazino]-1-propenylphenoxy)pentyloxy}-(11aS)-2,3,5,11$^a$-tetrahydro-5H-pyrrolo[2,1-c][1,4]benzo-diazepine-5-one (8d);

7-methoxy-8-{6-(2-methoxy-4-(E)-3-oxo-3-[4-(3,4,5-tri-methoxybenzoyl)piperazino]-1-propenylphenoxy)hexyloxy}-(11aS)-2,3,5,11$^a$-tetrahydro-5H-pyrrolo[2,1-c][1,4]benzo-diazepine-5-one (8e);

7-methoxy-8-{7-(2-methoxy-4-(E)-3-oxo-3-[4-(3,4,5-tri-methoxybenzoyl)piperazino]-1-propenylphenoxy)heptyloxy}-(11aS)-2,3,5,11$^a$-tetrahydro-5H-pyrrolo[2,1-c][1,4]benzo-diazepine-5-one (8f);

7-methoxy-8-{8-(2-methoxy-4-(E)-3-oxo-3-[4-(3,4,5-tri-methoxybenzoyl)piperazino]-1-propenylphenoxy)octyloxy}-(11aS)-2,3,5,11$^a$-tetrahydro-5H-pyrrolo[2,1-c][1,4]benzo-diazepine-5-one (8g);

7-methoxy-8-{9-(2-methoxy-4-(E)-3-oxo-3-[4-(3,4,5-tri-methoxybenzoyl)piperazino]-1-propenylphenoxy)nonyloxy}-(11aS)-2,3,5,11$^a$-tetrahydro-5H-pyrrolo[2,1-c][1,4]benzo-diazepine-5-one (8h);

7-methoxy-8-{10-(2-methoxy-4-(E)-3-oxo-3-[4-(3,4,5-tri-methoxybenzoyl)piperazino]-1-propenylphenoxy)decyloxy}-(11aS)-2,3,5,11$^a$-tetrahydro-5H-pyrrolo[2,1-c][1,4]benzo-diazepine-5-one (8i);

7-methoxy-8-(2-2-methoxy-4-[(E)-3-(4-methylpiperazino)-3-oxo-1-propenyl-phenoxy]ethoxy)-(11aS)-2,3,5,11$^a$-tetrahydro-5H-pyrrolo[2,1-c][1,4]benzodiazepine-5-one (11$^a$);

7-methoxy-8-(3-2-methoxy-4-[(E)-3-(4-methylpiperazino)-3-oxo-1-propenyl-phenoxy]propoxy)-(11aS)-2,3,5,11$^a$-tetrahydro-5H-pyrrolo[2,1-c][1,4]benzodiazepine-5-one (11b);

7-methoxy-8-(4-2-methoxy-4-[(E)-3-(4-methylpiperazino)-3-oxo-1-propenyl-phenoxy]butoxy)-(11aS)-2,3,5,11$^a$-tetrahydro-5H-pyrrolo[2,1-c][1,4]benzodiazepine-5-one (11e);

7-methoxy-8-(5-2-methoxy-4-[(E)-3-(4-methylpiperazino)-3-oxo-1-propenyl-phenoxy]pentyloxy)-(11aS)-2,3,5,11$^a$-tetrahydro-5H-pyrrolo[2,1-c][1,4]benzodiazepine-5-one (11d);

7-methoxy-8-(6-2-methoxy-4-[(E)-3-(4-methylpiperazino)-3-oxo-1-propenyl-phenoxy]hexyloxy)-(11aS)-2,3,5,11$^a$-tetrahydro-5H-pyrrolo[2,1-c][1,4]benzodiazepine-5-one (11e);

7-methoxy-8-(7-2-methoxy-4-[(E)-3-(4-methylpiperazino)-3-oxo-1-propenyl-phenoxy]heptyloxy)-(11aS)-2,3,5,11$^a$-tetrahydro-5H-pyrrolo[2,1-c][1,4]benzodiazepine-5-one (11f);

7-methoxy-8-(8-2-methoxy-4-[(E)-3-(4-methylpiperazino)-3-oxo-1-propenyl-phenoxy]octyloxy)-(11aS)-2,3,5,11$^a$-tetrahydro-5H-pyrrolo[2,1-c][1,4]benzodiazepine-5-one (11g);

7-methoxy-8-(9-2-methoxy-4-[(E)-3-(4-methylpiperazino)-3-oxo-1-propenyl-phenoxy]nonyloxy)-(11aS)-2,3,5,11$^a$-tetrahydro-5H-pyrrolo[2,1-c][1,4]benzodiazepine-5-one (11h);

7-methoxy-8-(10-2-methoxy-4-[(E)-3-(4-methylpiperazino)-3-oxo-1-propenyl-phenoxy]decyloxy)-(11aS)-2,3,5,11$^a$-tetrahydro-5H-pyrrolo[2,1-c][1,4]benzodiazepine-5-one (11i);

7-methoxy-8-(2-2-methoxy-4-[(E)-3-morpholino-3-oxo-1-propenylphenoxy]ethoxy)-(11aS)-2,3,5,11$^a$-tetrahydro-5H-pyrrolo[2,1-c][1,4]benzodiazepine-5-one (14$^a$);

7-methoxy-8-(3-2-methoxy-4-[(E)-3-morpholino-3-oxo-1-propenylphenoxy]propoxy)-(11aS)-2,3,5,11$^a$-tetrahydro-5H-pyrrolo[2,1-c][1,4]benzodiazepine-5-one (14b);

7-methoxy-8-(4-2-methoxy-4-[(E)-3-morpholino-3-oxo-1-propenylphenoxy]butoxy)-(11aS)-2,3,5,11$^a$-tetrahydro-5H-pyrrolo[2,1-c][1,4]benzodiazepine-5-one (14c);

7-methoxy-8-(5-2-methoxy-4-[(E)-3-morpholino-3-oxo-1-propenylphenoxy]pentyloxy)-(11aS)-2,3,5,11$^a$-tetrahydro-5H-pyrrolo[2,1-c][1,4]benzodiazepine-5-one (14d);

7-methoxy-8-(6-2-methoxy-4-[(E)-3-morpholino-3-oxo-1-propenylphenoxy]hexyloxy)-(11aS)-2,3,5,11$^a$-tetrahydro-5H-pyrrolo[2,1-c][1,4]benzodiazepine-5-one (14e);

7-methoxy-8-(7-2-methoxy-4-[(E)-3-morpholino-3-oxo-1-propenylphenoxy]heptyloxy)-(11aS)-2,3,5,11$^a$-tetrahydro-5H-pyrrolo[2,1-c][1,4]benzodiazepine-5-one (14f);

7-methoxy-8-(8-2-methoxy-4-[(E)-3-morpholino-3-oxo-1-propenylphenoxy]octyloxy)-(11aS)-2,3,5,11$^a$-tetrahydro-5H-pyrrolo[2,1-c][1,4]benzodiazepine-5-one (14g);

7-methoxy-8-(9-2-methoxy-4-[(E)-3-morpholino-3-oxo-1-propenylphenoxy]nonyloxy)-(11aS)-2,3,5,11a-tetrahydro-5H-pyrrolo[2,1-c][1,4]benzodiazepine-5-one (14h);

7-methoxy-8-(10-2-methoxy-4-[(E)-3-morpholino-3-oxo-1-propenylphenoxy]decyloxy)-(11aS)-2,3,5,11a-tetrahydro-5H-pyrrolo[2,1-c][1,4]benzodiazepine-5-one (14i);

1,1'-{[(E-3-bis ethoxy-3-methoxy phenyl)-1-4-piperzino]-2-propene-1-one}dioxy}bis(11aS)-7-methoxy-1,2,3,11$^a$-tetrahydro-5H-pyrrolo[2,1-c][1,4]benzo diazepine-5-one (17$^a$)

1,1'-{[(E-3-bis propoxy-3-methoxy phenyl)-1-4-piperzino]-2-propene-1-one}dioxy}bis(11aS)-7-methoxy-1,2,3,11a-tetrahydro-5H-pyrrolo[2,1-c][1,4]benzo diazepine-5-one (17b)

1,1'-{[(E-3-bis butoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17c)

1,1'-{[(E-3-bis pentyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17d)

1,1'-{[(E-3-bis hexyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17e)

1,1'-{[(E-3-bis heptyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17f)

1,1'-{[(E-3-bis octyloxy-3-methoxy phenyl)-1-4-piperzino]-2-propene-1-one}dioxy}bis(11aS)-7-methoxy-1,2,3,11a-tetrahydro-5H-pyrrolo[2,1-c][1,4]benzo diazepine-5-one (17g)

1,1'-{[(E-3-bis nonyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17h)

1,1'-{[(E-3-bis decyloxy-3-methoxy phenyl)-1-4-piperzino]-2-propene-1-one}dioxy}bis(11aS)-7-methoxy-1,2,3,11a-tetrahydro-5H-pyrrolo[2,1-c][1,4]benzo diazepine-5-one (17i)

In yet another embodiment the Cinnamido-pyrrolo[2,1-c][1,4]benzodiazepine hybrid 8b exhibits an in vitro anticancer/antitumour activity against human cancer cell lines selected from the group consisting of lung (Hop-62), cervix (SiHa), breast (MCF7, Zr-75-1), colon (Colo205), prostate (DU145, PC3) and oral (DWD, HT1080) cell lines.

In yet another embodiment the concentration of the compound 8b used for in vitro activity against leukemia cell line for GI50 is in the range of 0.02 to 0.65 μm, at an exposure period of at least 48 hrs.

In yet another embodiment the concentration of the compound 8b used for in vitro activity against lung cell line for GI50 is in the range of 0.17 to 3.07 μm, at an exposure period of at least 48 hrs.

In yet another embodiment the concentration of the compound 8b used for in vitro activity against colon cell line for GI50 is in the range of 0.18 to 3.39 μm, at an exposure period of at least 48 hrs.

In yet another embodiment the concentration of the compound 8b used for in vitro activity against CNS cell line for GI50 is in the range of 0.01 to 0.33 μm, at an exposure period of at least 48 hrs.

In yet another embodiment the concentration of the compound 8b used for in vitro activity against melanoma cell line for GI50 is in the range of 0.17 to 0.33 μm, at an exposure period of at least 48 hrs.

In yet another embodiment the concentration of the compound 8b used for in vitro activity against ovarian cell line for GI50 is in the range of 0.26 to 2.20 μm, at an exposure period of at least 48 hrs.

In yet another embodiment the concentration of the compound 8b used for in vitro activity against renal cell line for GI50 is in the range of 0.20 to 2.75 μm, at an exposure period of at least 48 hrs.

In yet another embodiment the concentration of the compound 8b used for in vitro activity against prostate cell line for GI50 is in the range of 0.34 to 1.47 μm, at an exposure period of at least 48 hrs.

In yet another embodiment the concentration of the compound 8b used for in vitro activity against breast cell line for IC50 is in the range of 0.13 to 0.31 μm, at an exposure period of at least 48 hrs.

The present invention further provides a process for preparation of cinnamido-pyrrolo[2,1-c][1,4]benzodiazepine hybrids of formulae 8a-i, 11a-i, 14a-i and 17a-i which comprises
  a) reacting (2S)—N-[(n-bromoalkyloxy)-3-methoxy-2-nitrobenzoyl)]pyrrolidine-2-carboxaldehyde diethylthioacetal of formula 1

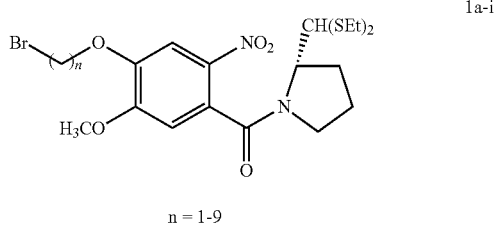

n = 1-9 with the compounds of formulae 2 or 3 or 4 or 5

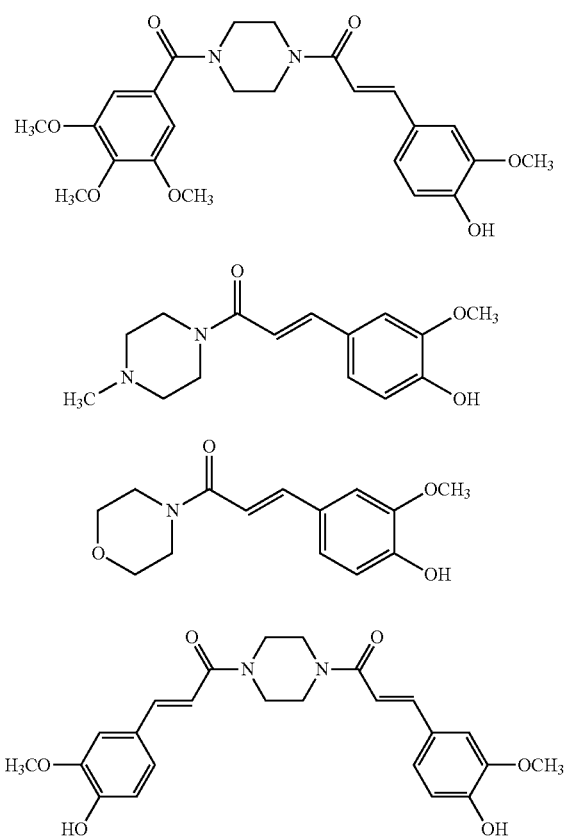

in an aprotic water miscible organic solvent, in the presence of anhydrous mild inorganic bases, like $K_2CO_3$, $BaCO_3$ and $CsCO_3$, under refluxing temperature in an oil bath, for a period of about 48 hrs, followed by the removal of inorganic base by filtration and evaporating the organic solvent to obtain the resultant crude product and purifying it by column chromatography to obtain the desired product of formulae 6a-i, 9a-i, 12a-i and 15a-i respectively,
  b) reducing the compounds of formulae 6a-i, 9a-i, 12a-i and 15a-i with $SnCl_2.2H_2O$, in an alcohol, under reflux, followed by the evaporation of alcohol and adjusting the pH of the resultant product layer to about 8 by using a base, followed by extraction with ethyl acetate and washing the combined organic phase with brine solution and evaporating the solvent to obtain the desired products of formulae 7a-i, 10a-i, 13a-i and 16a-i respectively,
  c) reacting the above said amino compounds of formulae 7a-i, 10a-i, 13a-i and 16a-i obtained in step (b) with a deprotecting agent by known method to obtain the desired compounds of formulae 8a-i, 11a-i, 14a-i and 17a-i respectively.

DETAILED DESCRIPTION OF THE INVENTION

The precursors cinnamides of formulae 2, 3, 4 and 5 have been prepared by well known method; 3,4,5-trimethoxy benzoic acid and cinnamic acid converted to corresponding acid chlorides by employing $SOCl_2$, 2 or 3 drops DMF in dry Benzene and then coupled to piperzine in presence of TEA in dry THF and accordingly (2S)-2-[di(ethylsulfanyl)methyl] tetrahydro-1H-1-pyrrolyl(4-hydroxy-5-methoxy-2-nitrophenyl)methanone of formula 1 (Thurston, D. E.; Murthy, V. S.; Langley, D. R.; Jones, G. B. *Synthesis*. 1990, 81) has been prepared by literature method.

Some representative compounds of formulae 8a-i, 11a-i and 17a-i for the present inventions are given below 7-methoxy-8-{n-(2-methoxy-4-(E)-3-oxo-3-[4-(3,4,5-trimethoxybenzoyl)piperazino]-1-propenylphenoxy) alkoxy}-(11aS)-2,3,5,11a-tetrahydro-5H-pyrrolo[2,1-c][1,4]benzodiazepine-5-one 8a-i;

7-methoxy-8-{n-2-methoxy-4-[(E)-3-(4-methylpiperazino)-3-oxo-1-propenylphenoxy]-alkoxy}-(11aS)-2,3,5,11a-tetrahydro-5H-pyrrolo[2,1-c][1,4]benzodiazepine-5-one 11a-i;

7-methoxy-8-{n-2-methoxy-4-[(E)-3-morpholino-3-oxo-1-propenylphenoxy]alkoxy}-(11aS)-2,3,5,11a-tetrahydro-5H-pyrrolo[2,1-c][1,4]benzodiazepine-5-one 14a-i;

1,1'-{[(E-3-bis alkoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one 17a-i.

These new analogues of pyrrolo[2,1-c][1,4]benzodiazepines linked at C-8 position have shown promising DNA binding activity and efficient anticancer activity in various cell lines. The molecules synthesized are of immense biological significance with potential sequence selective DNA-binding property. This resulted in design and synthesis of new congeners as illustrated in Scheme-1, which comprise:

1. The ether linkage at C-8 position of DC-81 intermediates with the compounds of formulae 2, 3, 4 and 5.
2. Refluxing the reaction mixtures for 48 h.
3. Synthesis of C-8 linked PBD antitumour antibiotic hybrid imines.
4. Purification by column chromatography using different solvents like ethyl acetate, hexane, dichloromethane and methanol.

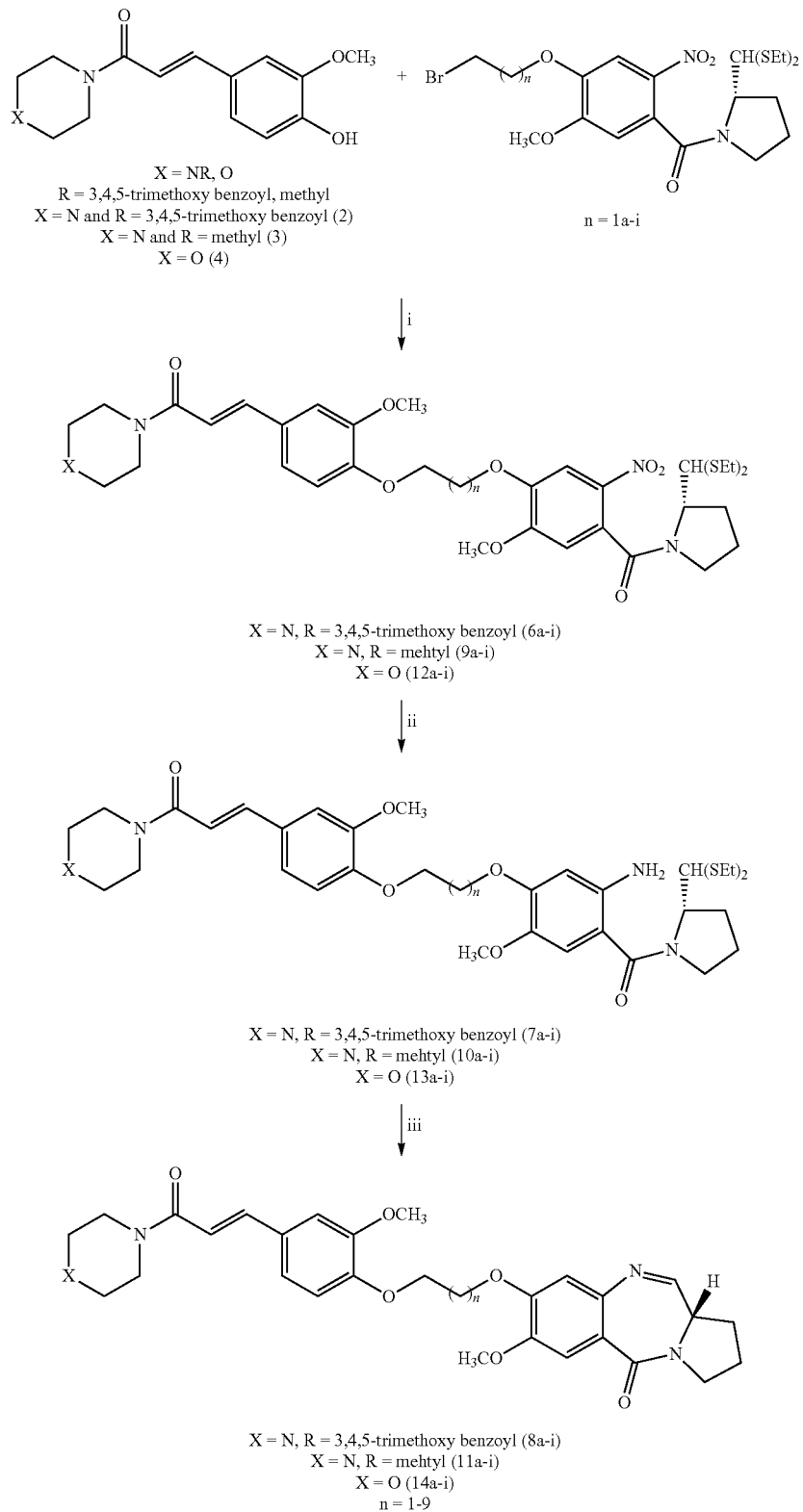
Reagents and conditions:
(i) K₂CO₃, acetone, 18 h, reflux, 65-73%;
(ii) SnCl₂•2H₂O, MeOH, 2 h, reflux, 86-88%;
(iii) HgCl₂—CaCO₃, CH₃CN—H₂O (4:1), 12 h, rt, 70-72%.

Scheme-2

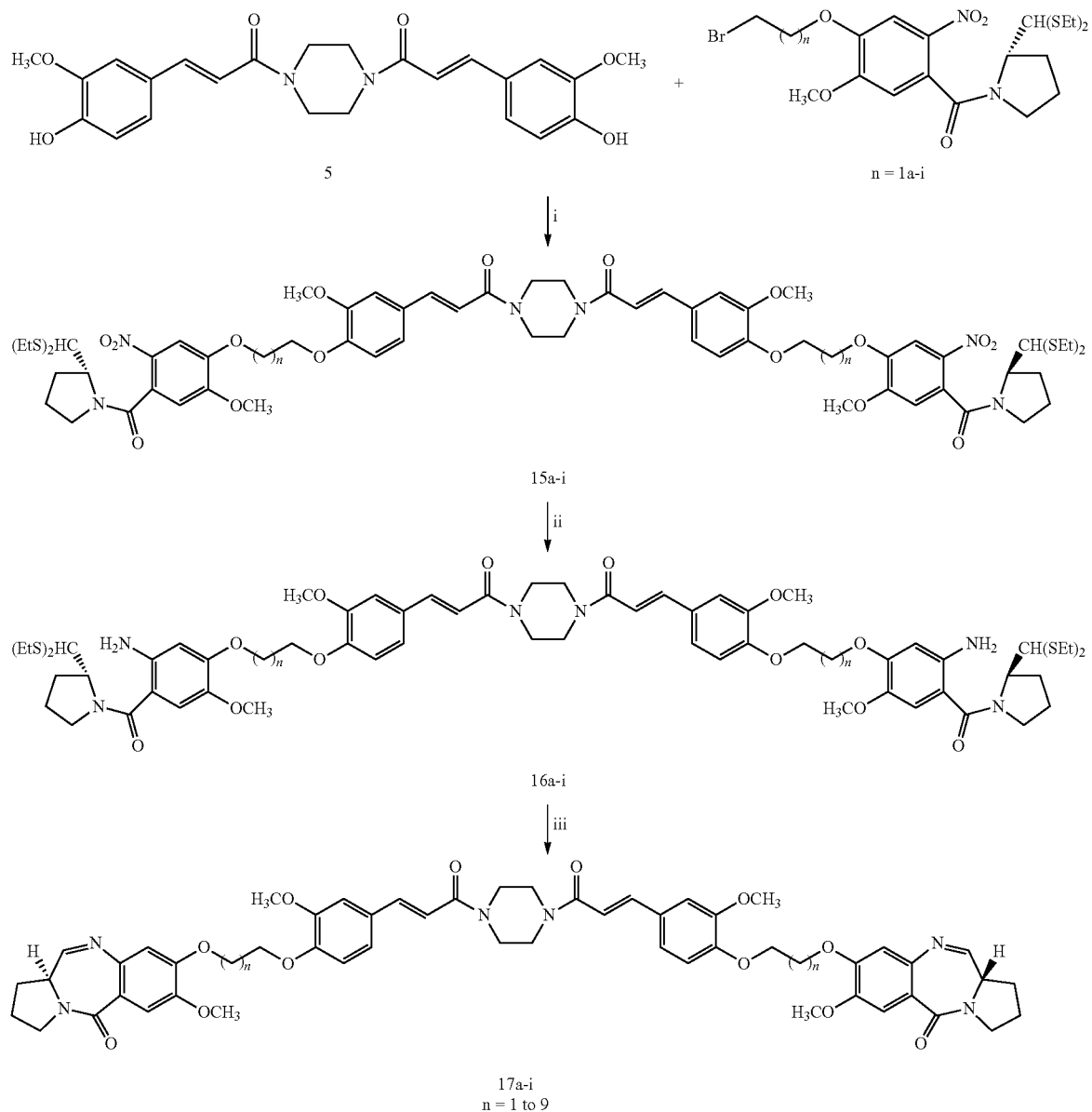

17a-i
n = 1 to 9

Reagents and conditions:
(i) K₂CO₃, acetone, 18 h, reflux, 88-91%;
(ii) SnCl₂·2H₂O, MeOH, 2 h, reflux, 85-87%;
(iii) HgCl₂—CaCO₃, CH₃CN—H₂O (4:1), 12 h, rt, 67-69%.

The following examples are given by way of illustration of the working of the invention in actual practice and therefore should not be construed to limit the scope of present invention in any way.

EXAMPLE-1

7-methoxy-8-{3-(2-methoxy-4-(E)-3-oxo-3-[4-(3,4, 5-trimethoxybenzoyl)piperazino]-1propenylphenoxy)propoxy}-(11aS)-2,3,5,11a-tetrahydro-5H-pyrrolo[2,1-c][1,4]benzo diazepine-5-one 8b To a solution of (2S)—N-[4-(3-bromopropyl)oxy-5-methoxy-2-nitrobenzoyl)pyrrolidine-2-carboxarbaldehyde diethylthioacetal 1b (500 mg, 1 mmol) in acetone (10 mL) was added anhydrous K₂CO₃ (528 mg, 4 mmol) and the (E)-3-(4-hydroxy-3-methoxyphenyl)-1-[4-(3,4,5-trimethoxybenzoyl) piperazino]-2-propen-1-one 2 (436 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using chlorofom-methanol (99: 1) as eluant to afford pure compound of 6b (580 mg, 67%).

¹H NMR (CDCl₃): δ 1.17-1.34 (m, 6H), 1.5-1.83 (m, 2H), 1.88-2.13 (m, 2H), 2.19-2.38 (m, 2H), 2.55-2.79 (m, 4H), 3.11-3.27 (m, 2H), 3.74 (s, 12H), 3.78-3.92 (m, 6H), 4.15-4.29 (m, 4H), 4.55-4.67 (m, 1H), 4.76 (d, 1H, J=3.77) 6.37 (d,

1H, J=15.1 Hz), 6.7 (s, 1H)), 4.7 (m, 1H), 6.75 (d, 1H, J=8.3 Hz), 6.86 (s, 1H), 6.96 (s, 1H), 7.15 (d, 1H, J=8.3 Hz), 7.59 (d, 1H, J=15.1 Hz), 8.52 (s, 1H).

ESIMS: m/z 898 ($M^+$+1).

To compound 6b (580 mg, 1 mmol) in methanol (20 mL) was added $SnCl_2.2H_2O$ (729 mg, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL) The combined organic phase was dried over $Na_2SO_4$ and evaporated under vacuum to afford the crude amino diethylthioacetal 7b (503 mg, 89%), which was used directly in the next step.

A solution of 7b (503 mg, 1 mmol), $HgCl_2$ (355 mg, 2.26 mmol) and $CaCO_3$ (142 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried over ($Na_2SO_4$). The organic layer was evaporated under vacuum and purified by column chromatography using $CHCl_3$-MeOH (5%) to give compound 8b (258 mg, 60%). This material was repeatedly evaporated, from $CHCl_3$ in vacuum to generate the imine form.

$^1H$ NMR ($CDCl_3$): δ 1.21-1.36 (m, 2H), 1.58-2.05 (m, 2H), 2.22-2.46 (m, 2H), 3.45-3.74 (m, 8H), 3.88 (s, 12H). 4.1-4.33 (t, 1H), 6.71 (d, 1H, J=15.63 Hz), 6.85 (d, 1H, J=7.03 Hz), 6.93 (s, 1H), 7.02 (s, 1H), 7.07 (d, 1H, J=7.03 Hz), 7.51 (s, 2H), 7.64 (d, 1H, 0.1=14.69 Hz), 7.67 (d, 1H, J=14.85 Hz)

FABMS: 743 ($M^+$+1).

EXAMPLE-2

7-methoxy-8-(3-2-methoxy-4-[(E)-3-(4-methylpiperazino)-3-oxo-1-propenylphenoxy]propoxy}-(11aS)-2,3,5,11a-tetrahydro-5H-pyrrolo[2,1-c][1,4]benzo diazepine-5-one 11b To a solution of (2S)—N-[4-(3-bromopropyl)oxy-5-methoxy-2-nitrobenzoyl)pyrrolidine-2-carboxarbaldehyde diethylthioacetal 1b (540 mg, 1 mmol) in acetone (10 mL) was added anhydrous $K_2CO_3$ (572 mg, 4 mmol) and the (E)-3-(4-hydroxy-3-methoxyphenyl)-1-(4-methylpiperazino)-2-propen-1-one 3 (286 mg, 1 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using $CHCl_3$-MeOH (2%) as eluent to afford pure compound of 9b (510 mg 68%)

$^1H$ NMR ($CDCl_3$): δ 1.17-1.36 (m, 6H), 1.41-1.52 (m, 2H), 1.91-2.20 (m, 2H), 2.26-2.50 (m, 2H), 2.62-2.83 (m, 4H), 3.20-3.33 (m, 4H), 3.61-3.74 (m, 8H), 3.88 (s, 6H), 4.24 (t, 2H J=6.15 Hz), 4.37 (t, 2H, J=6.15 Hz), 4.65-4.71 (m, 1H), 4.81 (d, 1H, J=3.76 Hz), 6.62 (d, 1H, J=15.28 Hz), 6.75 (s, 1H), 6.88 (d, 1H, J=8.26 Hz), 7.01 (s, 1H), 7.13 (d, 1H, J=8.26 Hz), 7.51 (d, 1H, J=15.28 Hz), 7.72 (s, 1H)

FABMS: m/z 717 ($M^+$).

To compound 9b (510 mg, 1 mmol) in methanol (20 mL) was added $SnCl_2.2H_2O$ (803 mg, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethylthioacetal 10b (424 mg, 87%), which was used directly in the next step.

A solution of 10b (424 mg, 1 mmol), $HgCl_2$ (378 mg, 2.26 mmol) and $CaCO_3$ (152 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$). The organic layer was evaporated under vacuum and purified by column chromatography using $CHCl_3$-MeOH (5%) to give compound 11b (201 mg, 58%). This material was repeatedly evaporated from $CHCl_3$ in vacuum to generate the imine form.

$^1H$ NMR ($CDCl_3$): δ 1.23-1.37 (m, 2H), 1.62-1.77 (t, 2H), 1.99-2.15 (m, 2H), 2.25-2.49 (m, 4H), 3:56-3.89 (m, 8H), 3.94 (s, 6H), 4.19-4.31 (t, 1H), 6.72 (d, 1H, J=15.83 Hz), 6.88 (s, 2H), 6.91 (d, 1H, J=8.30 Hz), 7.02 (s, 1H), 7.08 (d, 1H, J=8.30 Hz), 7.55 (d, 1H, J=18.22 Hz), 7.63 (d, 1H, J=5.78 Hz).

FABMS: m/z 563 ($M^+$+1).

EXAMPLE-3

7-methoxy-8-(3-2-methoxy-4-[(E)-3-morpholino-3-oxo-1-propenylphenoxy]propoxy}-(11aS)-2,3,5,11a-tetrahydro-5H-pyrrolo[2,1-c][1,4]benzodiazepine-5-one 14b To a solution of (2S)—N-[4-(5-bromopropyl)oxy-5-methoxy-2-nitrobenzoyl]pyrrolidine-2-carboxaldehyde diethylthioacetal 1b (600 mg, 1 mmol) in acetone (10 mL) was added anhydrous $K_2CO_3$ (646 mg, 4 mmol) and the (E)-3-(4-hydroxy-3-methoxyphenyl)-1-morpholino-2-propen-1-one (307 mg, 1 mmol). The reaction-mixture was heated to reflux for 48 h. After completion of the reaction as indicated by TLC, potassium carbonate was removed by suction filtration and the solvent was removed under vacuum. The crude product thus obtained was purified by column chromatography using $CHCl_3$-MeOH (2%) as eluant to afford pure compound of 12b (561 mg, 69%).

$^1H$ NMR ($CDCl_3$): δ 1.27-1.38 (m, 6H), 1.45-1.53 (m, 2H), 1.90-2.17 (m, 2H), 2.24-2.44 (m, 2H), 2.65-2.86 (m, 4H), 3.16-3.30 (m, 2H), 3.63-3.71 (m, 8H), 3.89 (s, 6H), 4.26 (t, 2H J=6.04 Hz), 4.35 (t, 2H, J=6.04 Hz), 4.64-4.71 (m, 1H), 4.83 (d, 1H, J=3.77 Hz), 6.65 (d, 1H, J=15.10 Hz), 6.77 (s, 1H), 6.85 (d, 1H, J=8.36 Hz), 6.99 (s, 1H), 7:03 (d, 1H, J=8.30 Hz), 7.54 (d, 1H, J=15.86 Hz), 7.70 (s, 1H).FABMS: m/z 695 ($M^+$).

To compound 12b (561 mg, 1 mmol) in methanol (20 mL) was added $SnCl_2.2H_2O$ (951 mg, 5 mmol) and refluxed for 5 h or until the TLC indicated that reaction was completed. The methanol was evaporated under vacuum, the aqueous layer was then carefully adjusted to pH 8 with 10% $NaHCO_3$ solution and then extracted with ethyl acetate and chloroform (2×30 mL and 2×30 mL). The combined organic phase was dried over $Na_2SO_4$ and evaporated under vacuum to afford the crude amino diethyl thioacetal 13b (455 mg, 85%), which was used directly in the next step.

A solution of 13b (455 mg, 1 mmol), $HgCl_2$ (516 mg, 2.26 mmol) and $CaCO_3$ (207 mg, 2.46 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% $NaHCO_3$ (20 mL), brine (20 mL) and the combined organic phase was dried ($Na_2SO_4$).

The organic layer was evaporated under vacuum and purified by column chromatography using MeOH—CHCl$_3$ (5%) to give compound 14b (221 mg, 60%). This material was repeatedly evaporated from CHCl$_3$ in vacuum to generate the imine form.

$^1$H NMR (CDCl$_3$): δ 1.21-1.35 (m, 2H), 1.60-1.78 (t, 2H), 1.97-2.13 (m, 2H), 2.23-2.46 (m, 4H), 3.54-3.82 (m, 8H), 3.93 (s, 6H), 4.20-4.33 (t, 1H), 6.70 (d, 1H, J=15.78 Hz), 6.85 (s, 2H), 6.90 (d, 1H, J=8.30 Hz), 7.01 (s, 1H), 7.07 (d, 1H, J=8.30 Hz), 7.55 (d, 1H, J=18.28 Hz), 7.64 (d, 1H, J=5.81 Hz).

FABMS: m/z 541 (M$^+$+1).

EXAMPLE-4

To a solution of (2S)—N-[4-(5-bromopropyl)oxy-5-methoxy-2-nitrobenzoyl]pyrrolidine-2-carboxaldehyde diethylthioacetal 1b (549 mg, 1 mmol) in acetone (10 mL) was added anhydrous K$_2$CO$_3$ (1104 mg, 8 mmol) and the (E)-3-(4-hydroxy-3-methoxyphenyl)-1-4-[(E)-3-(4-hydroxy-3-methoxyphenyl)-2-propenoyl]piperazino-2-propen-1-one 5 (560 mg, 2 mmol). The reaction mixture was heated to reflux for 48 h. After completion of the reaction as indicated by TLC, potassium carbonate was removed by suction filtration and the solvent was removed under vacuum. The crude product thus obtained was purified by column chromatography using CHCl$_3$-MeOH (3%) as eluant to afford pure compound of 15b (540 mg, 70%).

$^1$H NMR (CDCl$_3$): δ 1.24-1.40 (m, 12H), 1.53-1.58 (m, 4H), 1.71-2.15 (m, 4H), 2.30-2.91 (m, 4H), 2.63-2.88 (m, 8H), 3.13-3.32 (m, 4H), 3.66-3.90 (m, 8H), 3.92 (s, 12H,), 4.19-4.40 (m, 8H), 4.63-4.74 (m, 2H), 4.87 (d, 2H, J=3.67 Hz), 6.74 (d, 2H, J=15.42 Hz), 6.81 (s, 2H,), 6.92 (d, 2H, J=8.08 Hz), 7.06 (d, 2H, J=5.8 Hz), 7.66 (d, 2H, J=15.42 Hz), 7.72 (s, 2H), 8.12 (s, 2H).

FABMS: m/z 1319 (M$^+$).

To compound 15b (726 mg, 1 mmol) in methanol (20 mL) was added SnCl$_2$.2H$_2$O (2.125 g, 10 mmol) and refluxed for 5 h or until the TLC indicated that reaction was completed. The methanol was evaporated under vacuum, the aqueous layer was then carefully adjusted to pH 8 with 10% NaHCO$_3$ solution and then extracted with ethyl acetate and chloroform (2×30 mL and 2×30 mL). The combined organic phase was dried over Na$_2$SO$_4$ and evaporated under vacuum to afford the crude amino diethyl thioacetal 16b (574 mg, 80%), which was used directly in the next step.

A solution of 16b (686 mg, 1 mmol), HgCl$_2$ (1.26 g, 4.52 mmol) and CaCO$_3$ (492 mg, 4.92 mmol) in acetonitrile-water (4:1) was stirred slowly at room temperature for overnight. The reaction mixture was diluted with ethyl acetate (30 mL) filtered through a celite pad. The clear organic supernatant was extracted with saturated 5% NaHCO$_3$ (20 mL), brine (20 mL) and the combined organic phase was dried (Na$_2$SO$_4$). The organic layer was evaporated under vacuum and purified by column chromatography using MeOH—CHCl$_3$ (4%) to give compound 17b (325 mg, 55%). This material was repeatedly evaporated from CHCl$_3$ in vacuum to generate the imine form.

$^1$H NMR (CDCl$_3$): δ 1.35-1.51 (m, 4H), 1.70-2.15 (m, 4H), 2.25-2.80 (m, 4H), 3.03-3,22(m, 4H), 3.63-3.89 (m, 8H), 3.93 (s, 12H,), 4.15-4.30 (m, 8H), 4.66-4.79 (t, 2H), 6.71 (d, 2H, J=15.48 Hz), 6.83 (s, 2H,), 6.90 (d, 2H, J=7.80 Hz), 7.16 (d, 2H, J=7.80 Hz), 7.629 (d, 2H, 4.62 Hz), 7.68 (d, 2H, J=15.48 Hz), 7.70 (s, 2H), 8.06 (s, 2H).

FABMS: m/z 1013 (M$^+$+1).

Biological Activity:
DNA-Binding Ability of Novel Cinnamido-Pyrrolo[2,1-c][1,4]Benzo Diazepines
Thermal Denaturation Studies Compounds have been subjected to thermal denaturation studies with duplex-form calf thymus DNA (CT-DNA) using an modification of a reported procedure (Newman, M. S. Carcinog-compr. Surv. 1976, 1, 203; (b) Hecht, S. S.; Loy, M.; Hoffman, Carcinog-compr. Surv. 1976, 1, 325). Working solutions in aqueous buffer (10 mM NaH$_2$PO$_4$/Na$_2$HPO$_4$, 1 mM Na$_2$EDTA, pH 7.00+0.01) containing CT-DNA (100 μm in phosphate) and the PBD (20 μm) have been prepared by addition of concentrated PBD solutions in DMSO to obtain a fixed [PBD]/[DNA] molar ratio of 1:5. The DNA-PBD solutions have been incubated at 37° C. for 0 and 18 h prior to analysis. Samples have been monitored at 260 nm using a Beckman DU-800 spectrophotometer fitted with high performance temperature controller, and heated at 1° C. min$^{-1}$ in the 40-110° C. range. DNA helix→coil transition temperatures (T$_m$) have been obtained from the maxima in the d(A$_{260}$)/dT derivative plots. Drug-induced alterations in DNA melting behavior are given by: ΔT$_m$=T$_m$(DNA+PBD)−T$_m$(DNA alone), where the T$_m$ value for the PBD-free CT-DNA is 69.1±0.01. The fixed [PBD]/[DNA] ratio used has not resulted in binding saturation of the host DNA duplex for any compound examined.

The DNA binding activity for these Cinnamido-pyrrolo[2,1-c][1,4]benzodiazepines have been examined by thermal denaturation studies using calf thymus (CT) DNA. Melting studies show that these compounds stabilize the thermal helix→coil or melting stabilization (ΔT$_m$) for the CT-DNA duplex at pH 7.0, incubated at 37° C., where PBD/DNA molar ratio is 1:5. The data for the compounds 8b&d, 11b&d, 14b&d and 17b&d is included in Table 1 for comparison.

TABLE 1

Thermal denaturation data for Cinnamido-pyrrolo[2,1-c][1,4]benzodiazepines with calf thymus (CT) DNA

| PBD hybrids | [PBD]:[DNA] molar ratio[b] | (ΔT$_m$ ° C.)[a] after incubation at 37° C. for | |
|---|---|---|---|
| | | 0 h | 18 h |
| 8b | 1:5 | 1.2 | 2.1 |
| 8d | 1:5 | 1.5 | 2.5 |
| 11b | 1:5 | 4.0 | 5.0 |
| 11d | 1:5 | 7.9 | 8.8 |
| 14b | 1:5 | 3.0 | 4.2 |
| 14d | 1:5 | 7.1 | 8.2 |
| 17b | 1:5 | 4.0 | 5.1 |
| 17d | 1:5 | 8.1 | 9.2 |
| DC-81 | 1:5 | 0.3 | 0.7 |

[a]For CT-DNA alone at pH 7.00 ± 0.01, T$_m$ = 69.1° C. ± 0.01 (mean value from 10 separate determinations), all ΔT$_m$ values are ±0.1-0.2° C..
[b]For a 1:5 molar ratio of [PBD]/[DNA], where CT-DNA concentration = 100 μM and ligand concentration = 20 μM in aqueous sodium phosphate buffer [10 mM sodium phosphate + 1 mM EDTA, pH 7.00 ± 0.01].
Biological Activity: Some of in vitro biological activity studies were carried out at the National Cancer Institute, Marryland, USA. and Tata Fundamental Reasearch Institute, Mumbai, India.

In vitro Cytotoxicity

The compounds were evaluated for in vitro anticancer activity against sixty human tumour cells derived from nine cancer types (leukemia, non-small-cell lung, colon, CNS, melanoma, ovarian, prostate, and breast cancer) as shown in Table 1a. For each compound, dose response curves for each cell line were measured at a minimum of five concentrations at 10 fold dilutions. A protocol of 48 h continuous drug exposure was used and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The $Log_{10}$ $GI_{50}$ (concentration in mol/L causing 50% growth inhibition) values for Cinnamido-pyrrolo[2,1-c][1,4] benzodiazepine (8b) is listed in Table 2. The mean graph midpoint values of $log_{10}$ TGI and $log_{10}$ LC50 as well as $log_{10}$ GI50 for 8b are listed in Table 3. As demonstrated by mean graph pattern, compound 8b exhibits an interesting profile of activity and selectivity for various cell lines. The mean graph mid point of $log_{10}$ TGI and $log_{10}$ LC50 showed similar pattern to the $log_{10}$ GI50 mean graph mid points.

TABLE 1a

|  | $Log_{10}$ GI50 | $Log_{10}$ LC50 |
|---|---|---|
| Leukemia | −6.77 | −4.00 |
| Non-small-cell lung | −6.31 | −4.17 |
| Colon | −6.43 | −4.70 |
| CNS | −6.78 | −4.74 |
| Melanoma | −6.64 | −5.35 |
| Ovarian | −6.36 | −4.11 |
| Renal | −6.20 | −4.47 |
| Prostate | −6.44 | −4.22 |
| Breast | −6.51 | −4.70 | each cancer type represents the average of six to eight different cancer cell lines.

TABLE 2

In vitro cytotoxicity of compounds 8b in sixty cancer cell lines

| Cancer panel/cell line | $GI_{50}$ (μm) 8b |
|---|---|
| Leukemia |  |
| CCRF-CEM | 0.25 |
| HL-60(TB) | 0.25 |
| K-562 | 0.15 |
| MOLT-4 | 0.20 |
| RPMI-8226 | 0.65 |
| SR | 0.02 |
| Non-small cell lung |  |
| A549/ATCC | 0.48 |
| EKVX | 0.86 |
| HOP-92 | 0.32 |
| HOP-92 | 0.17 |
| NCI-H226 | 0.25 |
| NCI-H23 | 0.32 |
| NCI-H322M | 3.07 |
| NCI-H460 | 0.33 |
| NCI-H522 | 0.66 |
| Colon |  |
| COLO 205 | 0.18 |
| HCC-2998 | 0.36 |
| HCT-116 | 0.20 |
| HCT-15 | 3.39 |
| HT29 | 0.40 |
| KM12 | 0.28 |
| SW-620 | 0.19 |
| CNS |  |
| SF-268 | 0.32 |
| SF-295 | 0.01 |
| SF-539 | 0.25 |
| SNB-19 | 0.33 |
| SNB-75 | 0.26 |
| U251 | 0.27 |

TABLE 2-continued

In vitro cytotoxicity of compounds 8b in sixty cancer cell lines

| Cancer panel/cell line | $GI_{50}$ (μm) 8b |
|---|---|
| Melanoma |  |
| LOX IMVI | 0.18 |
| MALME-3M | 0.20 |
| M14 | 0.37 |
| SK-MEL-28 | 0.21 |
| Ovarian |  |
| IGROV1 | 0.27 |
| OVCAR-3 | 0.29 |
| OVCAR-4 | 2.20 |
| OVCAR-5 | 0.29 |
| OVCAR-8 | 0.26 |
| SK-OV-3 | 0.49 |
| Renal |  |
| 786-0 | 0.49 |
| A498 | 0.21 |
| ACHN | 2.75 |
| CAKI-1 | 1.12 |
| RXF 393 | 0.20 |
| SN12C | 0.33 |
| TK-10 | 0.69 |
| UO-31 | 1.15 |
| Prostate |  |
| PC-3 | 0.34 |
| DU-145 | 0.36 |
| Breast |  |
| MCF7 | 0.13 |
| NCI/ADR-RES | 1.47 |
| MDA-MB-231/ATCC | 0.23 |
| HS 578T | 0.31 |
| MDA-MB-435 | 0.17 |
| BT-549 | 0.13 |
| T-47D | 0.15 |
| MDA-MB-468 | 0.14 |
| Melanoma |  |
| SK-MEL-5 | 0.19 |
| UACC-257 | 0.27 |
| UACC-62 | 0.17 |

TABLE 3

$log_{10}$ $GI_{50}$, $log_{10}$ TGI and $log_{10}$ $LC_{50}$ mean graphs midpoints(MG_MID) of in vitro cytotoxicity data for the compound 8b. against human tumour cell lines.

| Compound | $Log_{10}$ $GI_{50}$ | $Log_{10}$ TGI | $Log_{10}$ $LC_{50}$ |
|---|---|---|---|
| 8b | −6.48 | −5.59 | −4.5 |

Significance of the Work Carried Out

The Cinnamido-pyrrolo[2,1-c][1,4]benzodiazepines that have been synthesized exhibited significant DNA-binding ability and showed cytotoxic activity against sixty human tumour cell lines.

Advantages Of The Invention

1. The present invention provides a new pyrrolo[2,1-c][1,4] benzodiazepine hybrids useful as antitumour agents.

2. It also provides a process for the preparation of novel pyrrolo[2,1-c][1,4]benzodiaze-pine hybrids.

We claim:
1. A compound of formula A

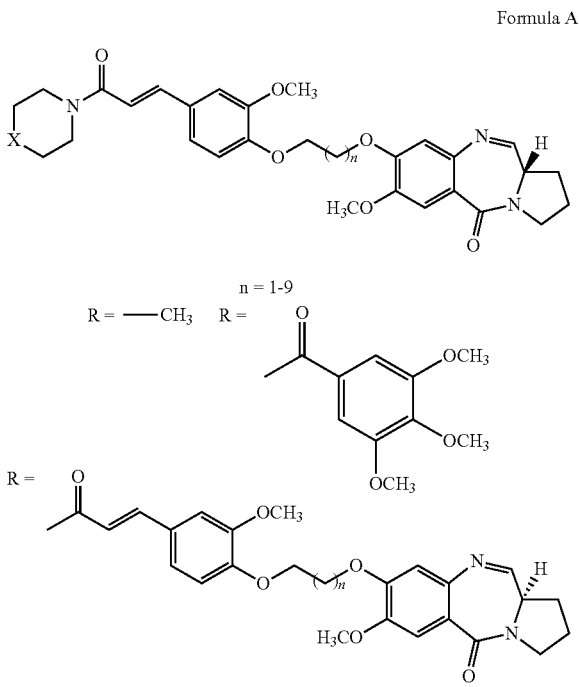

wherein X=O or NR.

2. The compound of claim 1 selected from the group consisting of:
- 7-methoxy-8-{2-(2-methoxy-4-(E)-3-oxo-3-[4-(3,4,5-tri-methoxybenzoyl)piperazino]-1-propenylphenoxy)ethoxy}-(11aS)-2,3,5,11a-tetrahydro-5H-pyrrolo[2,1-c][1,4]benzo-diazepine-5-one (8a);
- 7-methoxy-8-{3-(2-methoxy-4-(E)-3-oxo-3-[4-(3,4,5-tri-methoxybenzoyl)piperazino]-1-propenylphenoxy)propoxy}-(11aS)-2,3,5,11a-tetrahydro-5H-pyrrolo[2,1-c][1,4]benzo-diazepine-5-one (8b);
- 7-methoxy-8-{4-(2-methoxy-4-(E)-3-oxo-3-[4-(3,4,5-tri-methoxybenzoyl)piperazino]-1-propenylphenoxy)butoxy}-(11aS)-2,3,5,11a-tetrahydro-5H-pyrrolo[2,1-c][1,4]benzo-diazepine-5-one (8c);
- 7-methoxy-8-{5-(2-methoxy-4-(E)-3-oxo-3-[4-(3,4,5-tri-methoxybenzoyl)piperazino]1-propenylphenoxy)pentyloxy}-(11aS)-2,3,5,11a-tetrahydro-5H-pyrrolo[2,1-c][1,4]benzo-diazepine-5-one (8d);
- 7-methoxy-8-{6-(2-methoxy-4-(E)-3-oxo-3-[4-(3,4,5-tri-methoxybenzoyl)piperazino]-1-propenylphenoxy)hexyloxy}-(11aS)-2,3,5,11a-tetrahydro-5H-pyrrolo[2,1-c][1,4]benzo-diazepine-5-one (8e);
- 7-methoxy-8-{7-(2-methoxy-4-(E)-3-oxo-3-[4-(3,4,5-tri-methoxybenzoyl)piperazino]-1-propenylphenoxy)heptyloxy}-(11aS)-2,3,5,11a-tetrahydro-5H-pyrrolo[2,1-c][1,4]benzo-diazepine-5-one (8f);
- 7-methoxy-8-{8-(2-methoxy-4-(E)-3-oxo-3-[4-(3,4,5-tri-methoxybenzoyl)piperazino]-1-propenylphenoxy)octyloxy}-(11aS)-2,3,5,11a-tetrahydro-5H-pyrrolo[2,1-c][1,4]benzo-diazepine-5-one (8g);
- 7-methoxy-8-{9-(2-methoxy-4-(E)-3-oxo-3-[4-3,4,5-tri-methoxybenzoyl)piperazino]-1-propenylphenoxy)nonyloxy}-(11aS)-2,3,5,11a-tetrahydro-5H-pyrrolo[2,1-c][1,4]benzo-diazepine-5-one (8h);
- 7-methoxy-8-{10-(2-methoxy-4-(E)-3-oxo-3-[4-(3,4,5-trimethoxybenzoyl)piperazino]-1-propenylphenoxy)decyloxy}-(11aS)-2,3,5,11a-tetrahydro-5H-pyrrolo[2,1-c][1,4]benzo-diazepine-5-one (8l);
- 7-methoxy-8-(2-{2-methoxy-4-[(E)-3-(4-methylpiperazino)-3-oxo-1-propenyl-phenoxy]ethoxy}-(11aS)-2,3,5,11a-tetrahydro-5H-pyrrolo[2,1-c][1,4]benzodiazepine-5-one (11a);
- 7-methoxy-8-(3-{2-methoxy-4-[(E)-3-(4-methylpiperazino)-3-oxo-1-propenyl-phenoxy]propoxy}-(11aS)-2,3,5,11a-tetrahydro-5H-pyrrolo[2,1-c][1,4]benzodiazepine-5-one (11b);
- 7-methoxy-8-(4-{2-methoxy-4-[(E)-3-(4-methylpiperazino)-3-oxo-1-propenyl-phenoxy]butoxy}-(11aS)-2,3,5,11a-tetrahydro-5H-pyrrolo[2,1-c][1,4]benzodiazepine-5-one (11c);
- 7-methoxy-8-(5-{2-methoxy-4-[(E)-3-(4-methylpiperazino)-3-oxo-1-propenyl-phenoxy]pentyloxy}-(11aS)-2,3,5,11a-tetrahydro-5H-pyrrolo[2,1-c][1,4]benzodiazepine-5-one (11d);
- 7-methoxy-8-(6-{2-methoxy-4-[(E)-3-(4-methylpiperazino)-3-oxo-1-propenyl-phenoxy]hexyloxy}-(11aS)-2,3,5,11a-tetrahydro-5H-pyrrolo[2,1-c][1,4]benzodiazepine-5-one (11e);
- 7-methoxy-8-(7-{2-methoxy-4-[(E)-3-(4-methylpiperazino)-3-oxo-1-propenyl-phenoxy]heptyloxy}(11aS)-2,3,5,11a-tetrahydro-5H-pyrrolo[2,1-c][1,4]benzodiazepine-5-one (11f);
- 7-methoxy-8-(8-{2-methoxy-4-[(E)-3-(4-methylpiperazino)-3-oxo-1-propenyl-phenoxy]octyloxy}-(11aS)-2,3,5,11a-tetrahydro-5H-pyrrolo[2,1-c][1,4]benzodiazepine-5-one (11g);
- 7-methoxy-8-(9-{2-methoxy-4-[(E)-3-(4-methylpiperazino)-3-oxo-1-propenyl-phenoxy]nonyloxy}-(11aS)-2,3,5,11a-tetrahydro-5H-pyrrolo[2,1-c][1,4]benzodiazepine-5-one (11h);
- 7-methoxy-8-(10-{2-methoxy-4-[(E)-3-(4-methylpiperazino)-3-oxo-1-propenyl-phenoxy]decyloxy}-(11aS)-2,3,5,11a-tetrahydro-5H-pyrrolo[2,1-c][1,4]benzodiazepine-5-one (11i);
- 7-methoxy-8-(2-{2-methoxy-4-[(E)-3-morpholino-3-oxo-1-propenylphenoxy]}-(11aS)-2,3,5,11a-tetrahydro-5H-pyrrolo[2,1-c][1,4]benzodiazepine-5-one (14a);
- 7-methoxy-8-(3-{2-methoxy-4-[(E)-3-morpholino-3-oxo-1-propenylphenoxy]propoxy}-(11aS)-2,3,5,11a-tetrahydro-5H-pyrrolo[2,1-c][1,4]benzodiazepine-5-one (14b);
- 7-methoxy-8-(4-{2-methoxy-4-[(E)-3-morpholino-3-oxo-1-propenylphenoxy]butoxy}-(11aS)-2,3,5,11a-tetrahydro-5H-pyrrolo[2,1-c][1,4]benzodiazepine-5-one (14c);
- 7-methoxy-8-(5-{2-methoxy-4-[(E)-3-morpholino-3-oxo-1-propenylphenoxy]pentyloxy}-(11aS)-2,3,5,11a-tetrahydro-5H-pyrrolo[2,1-c][1,4]benzodiazepine-5-one (14d);
- 7-methoxy-8-(6-{2-methoxy-4-[(E)-3-morpholino-3-oxo-1-propenylphenoxy]hexyloxy}-(11aS)-2,3,5,11a-tetrahydro-5H-pyrrolo[2,1-c][1,4]benzodiazepine-5-one (14e);
- 7-methoxy-8-(7-{2-methoxy-4-[(E)-3-morpholino-3-oxo-1-propenylphenoxy]heptyloxy}-(11aS)-2,3,5,11a-tetrahydro-5H-pyrrolo[2,1-c][1,4]benzodiazepine-5-one (14f);
- 7-methoxy-8-(8-{2-methoxy-4-[(E)-3-morpholino-3-oxo-1-propenylphenoxy]octyloxy}-(11aS)-2,3,5,11a-tetrahydro-5H-pyrrolo[2,1-c][1,4]benzodiazepine-5-one (14g);
- 7-methoxy-8-(9-{2-methoxy-4-[(E)-3-morpholino-3-oxo-1-propenylphenoxy]nonyloxy}-(11aS)-2,3,5,11a-tetrahydro-5H-pyrrolo[2,1-c][1,4]benzodiazepine-5-one (14h);

7-methoxy-8-(10-{2-methoxy-4-[(E)-3-morpholino-3-oxo-1-propenylphenoxy]decyloxy}-(11aS)-2,3,5,11a-tetrahydro-5H-pyrrolo[2,1-c][1,4]benzodiazepine-5-one (14i);

1,1'-{[(E-3-bis ethoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17a)

1,1'-{[(E-3-bis propoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17b)

1,1'-{[(E-3-bis butoxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17c)

1,1'-{[(E-3-bis pentyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17d)

1,1'-{[(E-3-bis hexyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17e)

1,1'-{[(E-3-bis heptyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17f)

1,1'-{[(E-3-bis octyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17g)

1,1'-{[(E-3-bis nonyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17h) and 1,1'-{[(E-3-bis decyloxy-3-methoxy phenyl)-1-4-piperzino]-2-propene-1-one]dioxy}bis(11aS)-7-methoxy-1,2,3,11a-tetrahydro-5H-pyrrolo[2,1-c][1,4]benzo diazepine-5-one (17i).

3. A process for the preparation of Cinnamido-pyrrolo[2,1-c][1,4]benzodiazepines of formulae A:

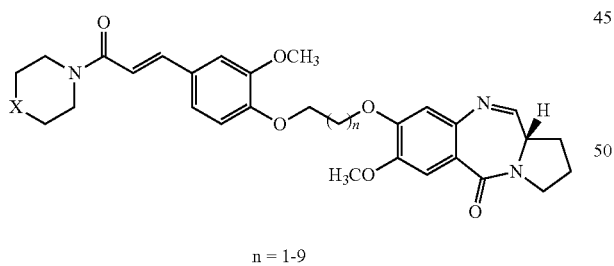

Formula A n = 1-9

Wherein X=O or NR

R = —CH$_3$  R =

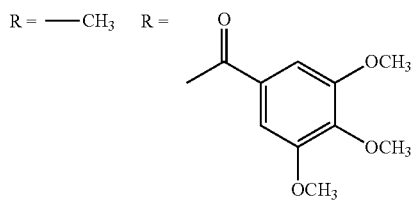

R =

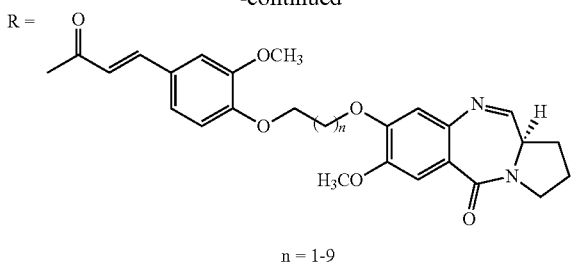

n = 1-9 comprising the steps of:
a) reacting [4-(n-bromoalkoxy)-5-methoxy-2-nitrophenyl](2S)-2-[di(ethylsulfanyl)methyl]tetrahydro-1H-1-pyrrolylmethanone of formula 1a-i

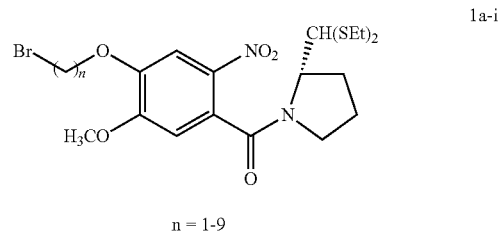

1a-i n = 1-9 with the cinnamides of formulae 2 or 3 or 4 or 5

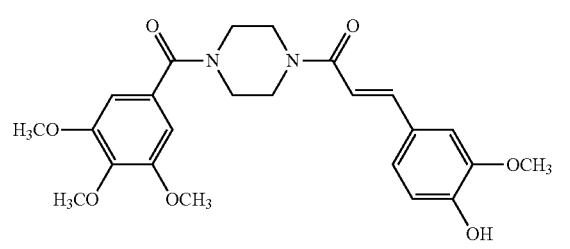

2

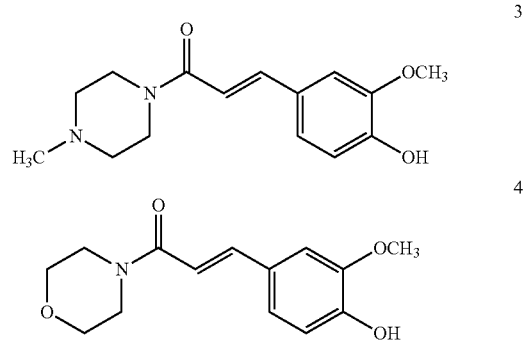

3

4

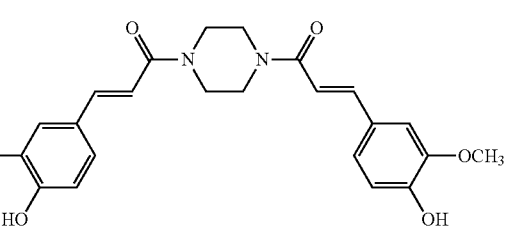

5 to obtain the nitro compounds of formulae 6a-i, 9a-i, 12a-i and 15a-i respectively

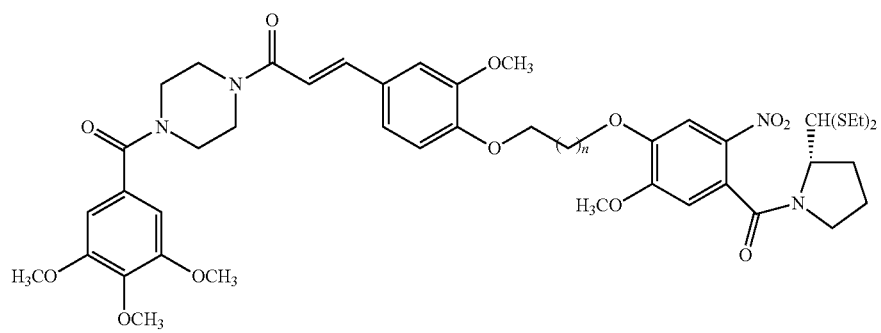
6a-i
n = 1-9
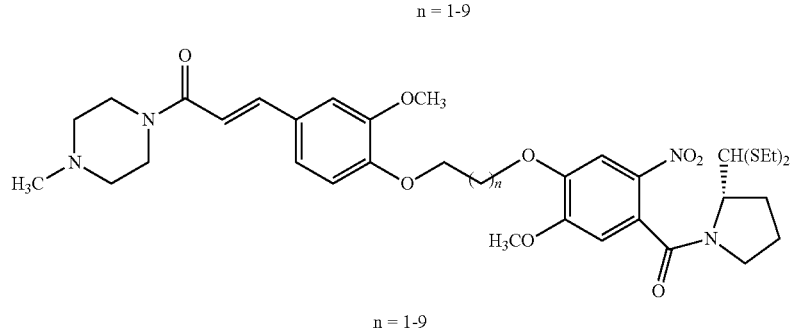
9a-i
n = 1-9
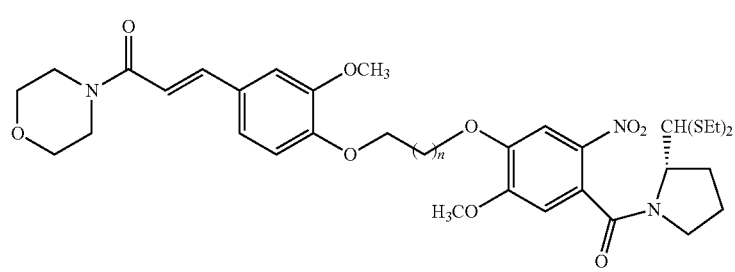
12a-i
n = 1-9
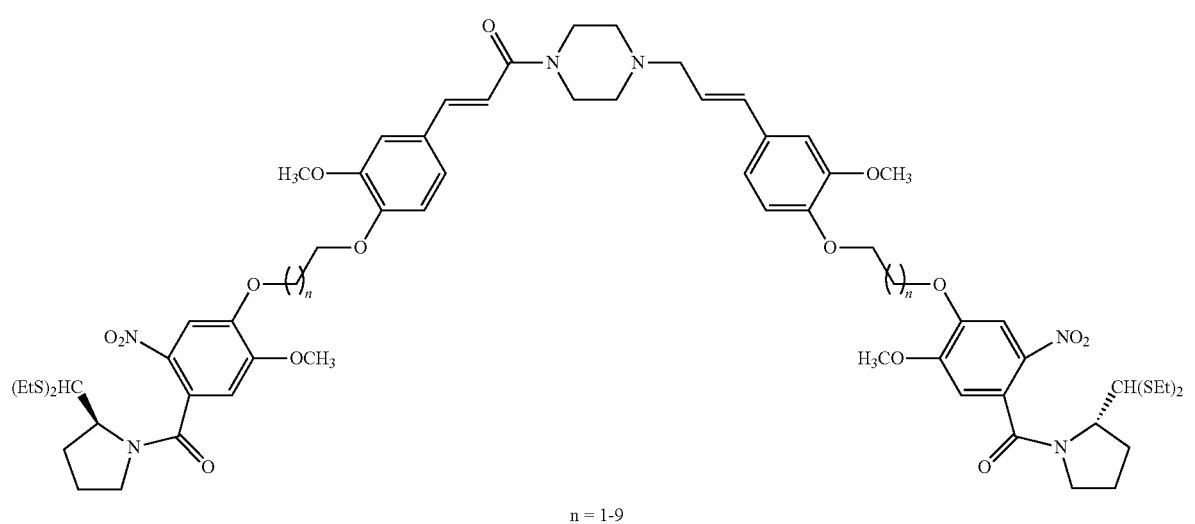
15a-i
n = 1-9
b) reducing the above nitro compounds of formulae 6a-i, 9a-i, 12a-i and 15a-i with SnCl$_2$.2H$_2$O in presence of organic solvent like methanol or ethanol up to a reflux temperature, obtaining the amino compounds of formulae 7a-i, 10a-i, 13a-i and 16a-i respectively,

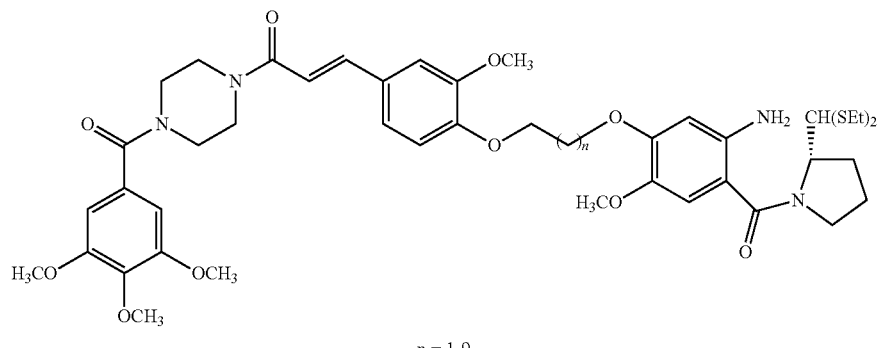
7a-i
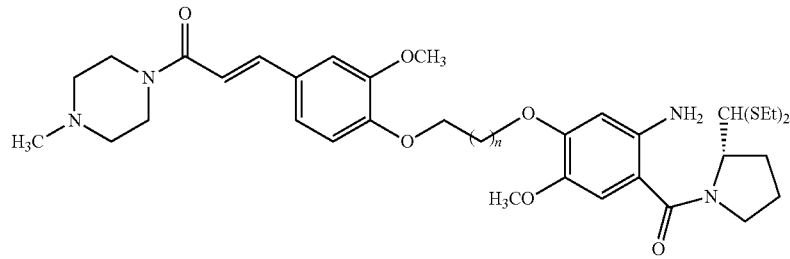
10a-i
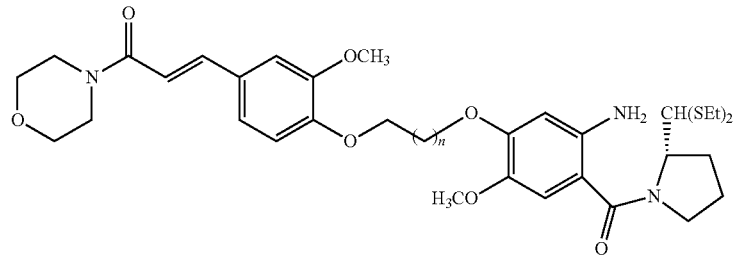
13a-i
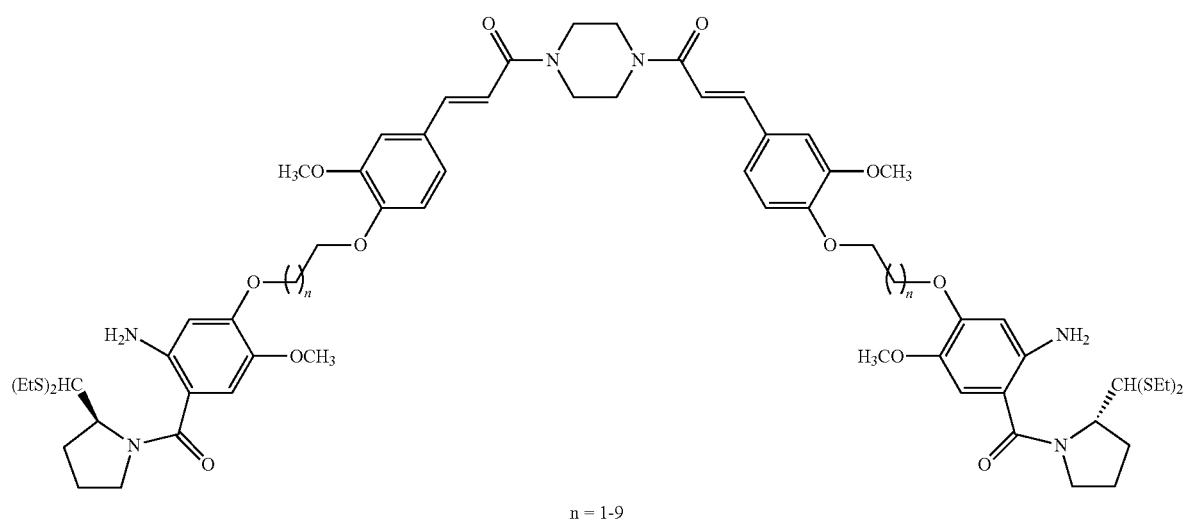
16a-i
c) reacting the above amino compounds of formulae 7a-i, 10a-i, 13a-i and 16a-i with known deprotecting agents to obtain Cinnamido-pyrrolo[2,1-c][1,4]benzodiazepines of formulae 8a-i, 11-a-i, 14a-i and 17a-i respectively.
* * * * *